United States Patent
Johannison

(10) Patent No.: US 9,486,366 B2
(45) Date of Patent: Nov. 8, 2016

(54) METHOD OF ATTACHING GRIP TABS TO THE CARRIER LAYER OF A FILM DRESSING

(75) Inventor: Ulf Johannison, Landvetter (SE)

(73) Assignee: Mölnlycke Health Care AB, Göteborg (SE)

( * ) Notice: Subject to any disclaimer, the term of this patent is extended or adjusted under 35 U.S.C. 154(b) by 772 days.

(21) Appl. No.: 13/498,593

(22) PCT Filed: Aug. 19, 2010

(86) PCT No.: PCT/SE2010/050897
§ 371 (c)(1),
(2), (4) Date: Mar. 28, 2012

(87) PCT Pub. No.: WO2011/040860
PCT Pub. Date: Apr. 7, 2011

(65) Prior Publication Data
US 2012/0184891 A1  Jul. 19, 2012

(30) Foreign Application Priority Data
Sep. 30, 2009  (SE) ...................................... 0950711

(51) Int. Cl.
*A61F 13/02* (2006.01)
*A61F 13/00* (2006.01)

(52) U.S. Cl.
CPC ......... *A61F 13/0289* (2013.01); *A61F 13/022* (2013.01); *A61F 13/024* (2013.01); *A61F 13/0236* (2013.01); *A61F 2013/008* (2013.01); *A61F 2013/00817* (2013.01)

(58) Field of Classification Search
USPC ............ 602/48–52; 428/40.1, 41.8; 156/498
See application file for complete search history.

(56) References Cited

U.S. PATENT DOCUMENTS

| | | | |
|---|---|---|---|
| 3,420,727 A | 1/1969 | Beck | 156/498 |
| 4,485,809 A | 12/1984 | Dellas | |

(Continued)

FOREIGN PATENT DOCUMENTS

| | | |
|---|---|---|
| AU | 2010301154 | 4/2012 |
| CA | 2771801 | 4/2011 |

(Continued)

OTHER PUBLICATIONS

International Preliminary Report on Patentability issued Apr. 3, 2012 for International Application No. PCT/SE2010/050897, which was filed on Aug. 19, 2010 and which was published as WO 2011/040860 on Apr. 7, 2011 (Inventor-Johannison; Applicant-Molnlycke Health Care AB) (pp. 1-6).

(Continued)

*Primary Examiner* — Ophelia A Hawthorne
(74) *Attorney, Agent, or Firm* — Ballard Spahr LLP

(57) ABSTRACT

A method is provided to attach a grip tab along an edge of a carrier layer of a film dressing web, which includes a film layer coated with adhesive on a first side and a carrier layer releasably attached to the film layer on an opposed second side. The method includes choosing a material for the carrier layer that is heat welding incompatible with the film layer, feeding the web in a machine direction, applying a first strip of a material that is heat welding compatible with the carrier layer along part of an edge portion of the web extending parallel to the machine direction, and affixing the first strip to the carrier layer while simultaneously cutting away an outermost part of the web with the first strip applied thereto by passing the web through an ultrasonic welding device.

10 Claims, 2 Drawing Sheets

(56) References Cited

U.S. PATENT DOCUMENTS

| | | | |
|---|---|---|---|
| 4,545,371 A | 10/1985 | Grossmann et al. | |
| 4,600,001 A | 7/1986 | Gilman | |
| 4,884,563 A | 12/1989 | Sessions | |
| 5,160,315 A | 11/1992 | Heinecke et al. | |
| 5,437,622 A | 8/1995 | Carion | 602/57 |
| 5,520,629 A * | 5/1996 | Heinecke et al. | 602/57 |
| 5,662,925 A * | 9/1997 | Ebert et al. | 424/447 |
| 5,738,642 A | 4/1998 | Heinecke | 602/58 |
| 5,948,208 A | 9/1999 | Speich | 156/580.2 |
| 6,495,230 B1 * | 12/2002 | do Canto | 428/41.8 |
| 7,049,479 B2 * | 5/2006 | Cleary et al. | 602/57 |
| 2004/0018329 A1 | 1/2004 | Katoh | 428/40.1 |
| 2004/0143220 A1 * | 7/2004 | Worthley | 604/174 |
| 2009/0105670 A1 | 4/2009 | Bentley et al. | |
| 2010/0331785 A1 * | 12/2010 | Fabo et al. | 604/180 |
| 2011/0020426 A1 * | 1/2011 | Baird et al. | 424/449 |

FOREIGN PATENT DOCUMENTS

| | | |
|---|---|---|
| CN | 102573721 | 7/2012 |
| DE | 4314834 A1 | 11/1994 |
| EP | 0066899 | 12/1982 |
| EP | 0161865 | 11/1985 |
| EP | 0189999 | 8/1986 |
| EP | 0401949 | 12/1990 |
| EP | 0985391 A2 | 3/2000 |
| EP | 2482774 | 8/2012 |
| GB | 791267 A | 2/1958 |
| GB | 1007573 | 10/1965 |
| JP | 2008-220395 A | 9/2008 |
| JP | 2008-264170 A | 11/2008 |
| WO | WO 95/00097 | 1/1995 |
| WO | WO 98/17216 | 4/1998 |
| WO | WO 98/52505 | 11/1998 |
| WO | WO 00/33776 | 6/2000 |
| WO | WO 2006/010961 | 2/2006 |
| WO | WO 2011/040860 | 4/2011 |

OTHER PUBLICATIONS

International Search Report and Written Opinion issued Jan. 11, 2011 for International Application No. PCT/SE2010/050897, which was filed on Aug. 19, 2010 and which was published as WO 2011/040860 on Apr. 7, 2011 (Inventor-Johannison; Applicant-Molnlycke Health Care AB) (pp. 1-11).

* cited by examiner

METHOD OF ATTACHING GRIP TABS TO THE CARRIER LAYER OF A FILM DRESSING

CROSS-REFERENCE TO RELATED APPLICATIONS

The present application is a U.S. National Phase Application of International Application No. PCT/SE2010/050897, filed Aug. 19, 2010, which claims priority to Swedish Patent Application No. 0950711-2, filed Sep. 30, 2009, all of which applications are incorporated herein fully by this reference.

TECHNICAL FIELD

The invention relates to a method of attaching a grip tab to at least one of two opposite edges of a releasable carrier layer of a film dressing web, said web includes a film layer on a first side coated with adhesive and a carrier layer releasably attached to the film layer on a second side thereof being opposite to the first side, the film layer and the carrier layer having the same dimensions, and a film dressing manufactured by said method.

BACKGROUND TO THE INVENTION

Film dressings consist in use of a thin plastic film coated with an adhesive. Due to its thin nature it is almost impossible to apply such an adhesively coated film. For this reason film dressings are provided with releasable carrier layers which stiffen up the film and make it possible to apply the film dressing in an easy manner as well as to cut the dressing in suitable pieces. The carrier layer may be a continuous layer covering the whole film but it can as well have the shape of a frame, whereby the central part of the film is uncovered. If the film further is transparent the dressing can more easily be applied to the wound. The carrier layer is removed after the film dressing is applied.

In order to facilitate the removal of the carrier layer grip tabs are often provided on the carrier layer. A problem with providing grip tabs is that the forces created when the grip tab is gripped have to act on an edge of the carrier layer. Otherwise there is a risk that a lifting of a grip tab will entail also a lifting of a part of the applied film of the dressing. A known way of solving this problem is to let the grip tab extend sideways from the edge of the dressing. However, grip tabs extending outside the dressing make the packaging of the dressing more complicated and the resulting package less aesthetically attractive.

The objective of the invention is to provide well functioning grip tabs on film dressings, which grip tabs do not extend outside the edges of the dressing.

SUMMARY OF THE INVENTION

This objective is accomplished by a method of attaching a grip tab to at least one of two opposite edges of a releasable carrier layer of a film dressing web, said web includes a film layer on a first side coated with adhesive and a carrier layer releasably attached to the film layer on a second side thereof being opposite to the first side, the film layer and the carrier layer having the same dimensions, characterised by the steps of, choosing a material for the carrier layer that is incompatible with the film layer from a heat welding point of view, feeding said film dressing web in a machine direction, applying a strip of a material compatible with the carrier layer from a heat welding point of view along at least a part of an edge portion of at least one of the opposite sides of said web extending parallel to the machine direction, and affixing said at least one strip to the carrier layer and simultaneously cutting away an outermost part of the web with the at least one strip applied thereto by passing the web with the at least one strip applied thereto through an ultrasonic welding device.

In a preferred embodiment of the method the at least one strip of material is preferably continuous and a release layer of thermoplastic material can be attached to the adhesive coating on the film layer before the step of applying a strip of material to the carrier layer.

Simultaneously to applying the strip applied along at least an edge portion of at least one of the opposite sides of said web, one or more strips of a material compatible with the carrier layer from a heat welding point of view can be applied between the two opposite edges of the carrier layer extending parallel to the machine direction, and simultaneously with the affixing of the strip applied along at least an edge portion of at least one of the opposite sides of said web, the strip(s) applied between the two opposite edges of the carrier layer is (are) affixed to the carrier layer and simultaneously with the affixing of said strips, said film dressing web is cut by passing the web with said strip(s) applied thereto through an ultrasonic welding device, the cutting line in each said strip applied between the two opposite edges of the carrier layer being located between the two opposite edges of said strip being parallel to the machine direction.

The invention also relates to a film dressing including a film layer on a first side coated with adhesive, a carrier layer releasably attached to the film layer on a second side thereof being opposite to the first side, and a release layer releasably attached to the adhesive coating, the film layer, the carrier layer and the release layer having the same dimensions, characterised by a grip tab extending inwardly over the carrier layer from a first edge of the dressing and being affixed to the carrier layer by a seam having its outermost part in line with said first edge.

In a preferred embodiment a grip tab is extending inwardly over the carrier layer also from a second edge of the dressing opposite to the first edge and is affixed to the carrier layer with a seam having its outermost part in line with said second edge. Each grip tab can be made of the same material as the carrier layer or of a different material.

The carrier layer can be made of polypropylene and the film layer of polyurethane.

The adhesive coating consists to advantageously of silicone adhesive and the release layer consists then of polyethylene.

The width of the weld seam is less than 1 mm.

BRIEF DESCRIPTION OF THE DRAWING

The invention will now be described with reference to the enclosed figures, of which.

DESCRIPTION OF EMBODIMENTS

The present invention is built on the insight that grip tabs affixed to a carrier layer of a film dressing and extending inwards over the carrier layer from an edge thereof must be fixed exactly along this edge if the risk for lifting an applied film when trying to remove the carrier layer should be eliminated. However, to apply a strip of material with its outer edge coincident with the edge of the carrier layer which is necessary if no part of the strip should extend outwardly of this edge, requires a lot of precision. Likewise is it difficult to provide a seam that follows the edge of the carrier layer. Such high demands of accuracy result in a slow production rate and sophisticated equipment for the manufacture of film dressings.

To allow attaching of such grip tabs without the need for sophisticated equipment or a slowing down of normal production rate for film dressings, the method according to the invention includes the step of cutting away the outermost portion(s) of a film dressing web after or in connection with affixing a strip of material by a seam along the side edge of the web but inwards thereof. By cutting away the outermost portion of the web, it is ensured that the edge of the outermost portion of the grip tab will be coincident with the outermost portion of the carrier layer. No great demand of accuracy in applying the material strips which after the cutting step will constitute the grip tabs, is required since the outermost portion of the strips will be cut away. If the cutting is made after the seam is provided also an outermost portion of the seam is cut away. Since the seam will be placed inwards of the edge of the uncut film dressing web it is easier to produce than a seam that should have its outermost portion coincident with the edge of the carrier layer.

Figure 1:
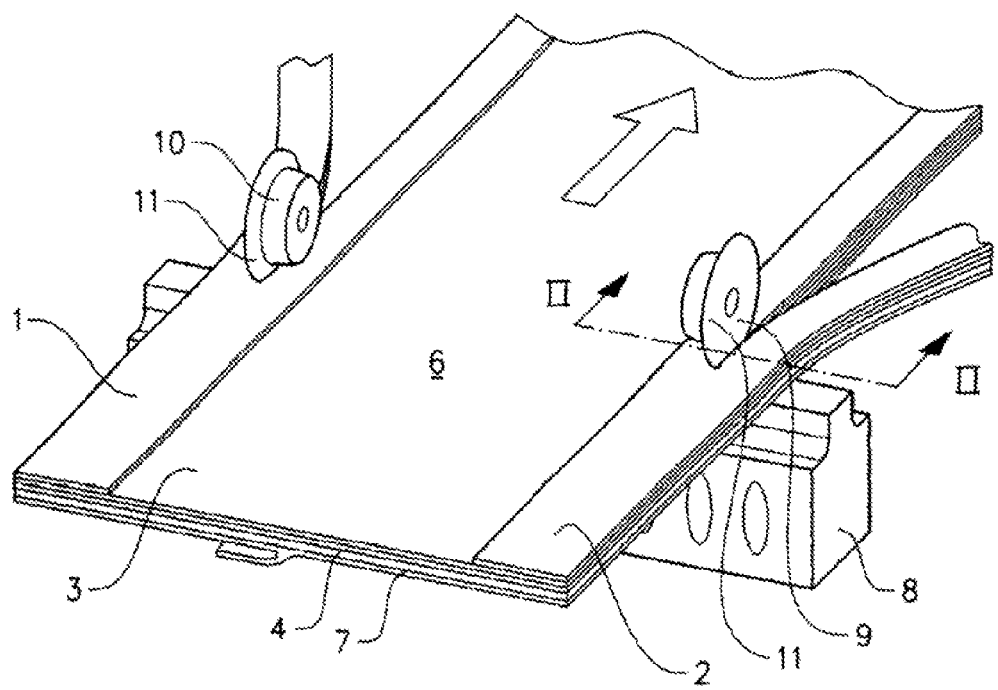
FIG. 1 shows a schematic perspective view from above of a part of an apparatus for attaching grip tabs to a film dressing according to a preferred embodiment of the invention.
Figure 2:
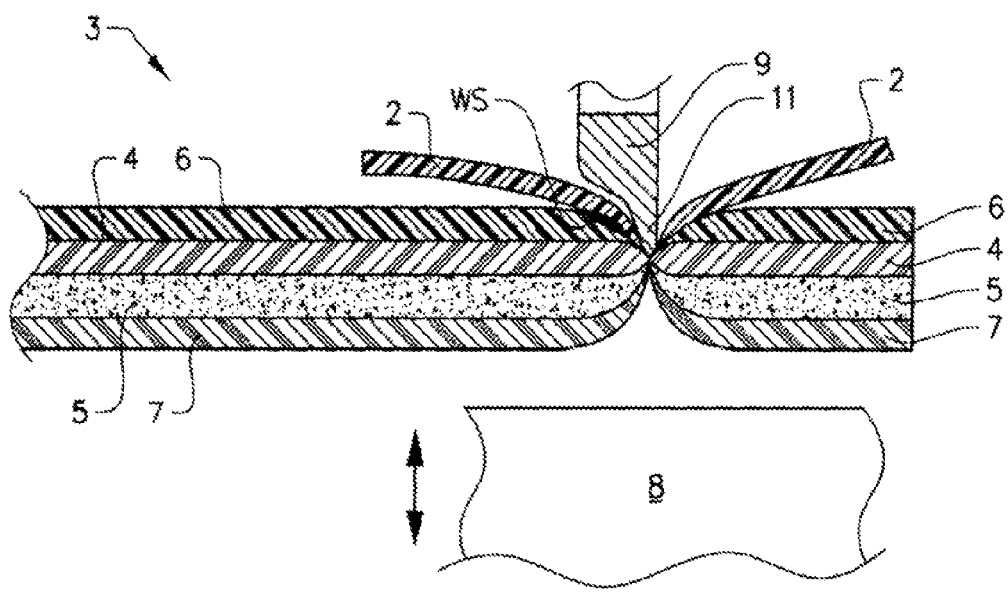
FIG. 2 shows a cross sectional view along line II-II in FIG. 1, and FIGS. 3 and 4 disclose similar views as FIGS. 1 and 2 of a second embodiment of the invention.

According to the invention, the cutting is performed simultaneously with the forming of the seam affixing the grip tab to the carrier layer. In FIGS. 1 and 2 a part of the equipment for attaching a grip tab to the carrier layer of a film dressing in accordance with the preferred embodiment of the invention is schematically shown.

The method according to the invention can easily be performed without sophisticated equipment and without influencing the normal production rate of film dressings. In the method step illustrated in FIG. 1, two continuous strips of heat weldable material 1,2 has been drawn from two rollers (not shown) and laid onto a film dressing web 3, the strips 1,2 extending along the two opposite edges thereof. Web 3 includes a film layer 4 having a thickness of 60 micrometer or less, which is coated with a layer of adhesive 5 on one side thereof. On the side of the web 3 opposite to the adhesively coated side a carrier layer 6 is releasably attached to the film layer 4. A release layer 7 has also been applied covering the adhesive layer for protection thereof before use of the dressing.

If the film 4 is bought from a supplier it is usually delivered with a stiffening layer coextruded with the film during manufacture thereof. Such a stiffening layer makes it possible to handle the film during manufacture, storing and transport. Such a stiffening layer can to advantage be used as carrier layer in a film dressing but it is of course possible to substitute it with another layer. Such a carrier layer can be releasably attached to the film layer for example by application of heat and pressure or application of a suitable adhesive.

After the two strips 1,2 have been laid onto the web 3, the web3 and the applied strips 1,2 pass in the machine direction through a ultrasonic welding device, the machine direction illustrated by an arrow in FIG. 1. The ultrasonic welding device is schematically shown in the figures by a horn 8 and counter rollers 9,10. The ultrasonic welding device cuts away the outermost portions of the film dressing web 3 and the applied strips 1,2 and simultaneously produces a weld seam WS along each of the cut edges. The strips 1,2 is thereby affixed to the carrier layer 6 with the outermost portion of each of the strips 1,2 and the seams WS coincident with the cut edge of the web 3.

In order to simultaneously produce a cutting and weld seam, the counter rollers 9, 10 each have a circumferential flange 11 on their outermost sides. When the horn 8 during its movement back and forth from the counter rollers 9,10, presses the web 3 and the applied strips 1,2 against the respective counter roller, material located under the flange 11 will be subjected to a higher degree of mechanical deformation than the material located under the remaining part of the respective counter roller. Accordingly more heat will be produced in the material under the respective flange than in the material under the remaining part of the respective counter roller. The counter rollers are constructed so that the material under the flange part of the rollers will melt away so that a cutting occur while the material under the remaining part of the rollers will soften to such a degree that the strips 1,2 will fuse together with the carrier layer 6. The materials in layers 4 and 7 will also soften and in order to prevent fusing together of layers 6 and 4 and 4 and 7, these materials should be incompatible to each other from a welding point of view.

The film layer 4 is preferably of polyurethane and the carrier layer 6 of polypropylene, materials which are incompatible to each other from a welding point of view, i.e. they do not fuse together when softened.

The adhesive coating is preferably a silicone gel adhesive and the release layer 7 is preferably made of polyethylene. If another adhesive, for example an acrylate adhesive is used, a release layer of for example silicon coated paper, or silicone coated polyethylene could be used. If silicone coated paper is used as a release layer, this should be applied after the film dressing web has passed the ultrasonic welding device. In such a case, a process layer of thermoplastic material is applied to cover the adhesive coating until the film dressing web has passed the ultrasonic welding device in order to prevent adhesive from adhering to the horn of the ultrasonic welding device. This process layer is then substituted by the release paper layer. In order to facilitate the manufacturing process a release layer made of a thermoplastic material is preferred.

The continuous strips 1,2 can be preferably be made of the same material as the carrier layer to assure good weldability there between but other materials, such as elastic polyolefin-based films, e.g. ethylene-vinyl-alcohol, having good weldability to the polypropylene in the carrier layer 6 can also be used.

Other combinations of thermoplastic materials for layers 4,6, land strips 1,2 having poor weldability to each other can also be used in the present invention. Polyester can for example be used as an alternative to polypropylene.

After having passed the ultrasonic welding device 8-10, distinct film dressings are made by cross-wise cutting of the web 3 and the applied grip tabs 1,2 and then be brought into neat packages in which the grip tabs are protected from wrinkling and other deformation due to packaging and later handling of the packages made. By such protection it is also ensured that the grip tabs not unintentionally can be gripped during handling of the package of film dressings, such unintentional gripping can lead to local release of the carrier layer from the film layer.

Instead of cross-wise cutting, the web 3 with the applied grip tabs 1,2 can be wound on a storage roller, thereby forming a film dressing of the type in which separate film dressings with a desired shape or dimension can be cut out by the user and still having at least one grip tab if at least a portion of one edge of the web 3 is present in the cut out film dressing. Also the film dressings made by cross-wise cutting of the web 3 can of course be cut into any desired shape.

In the preferred embodiment, the grip tabs 1,2 extend along the total length of two opposite edge portions of the manufactured film dressing(s). However, it is of course possible but not preferred to instead of applying continuous strips 1,2 apply a row of separate strips along each of the two opposite edges of the web 3, thereby obtaining grip tabs which only extend along a part of the length of the edges of the produced film dressings. It is of course also possible to only apply a strip along one of the two opposite sides of web 3, but this is not preferred.

The width of the seam WS formed between a grip tab 1,2 and the carrier layer 6 should not exceed 1 mm in the produced film dressing and the inward extension of the grip tab 1,2 over the carrier layer should preferably be at least 10 mm to facilitate easy handling thereof.

In order to mark the grip tabs for the user these can have different colour than the carrier layer or/and a different structure, for example obtained by embossing.

The radial and axial dimensions of the counter rollers 9, 10 to obtain the desired weld seam and cutting line depend on the thickness of the material passing through the ultrasonic welding device, the type of thermoplastic materials involved, the transport rate of the web and the frequency of the ultra sonic horn. However, suitable counter rollers can easily be chosen or constructed by the skilled man on basis of desired values for the parameters mentioned above.

Figure 3:
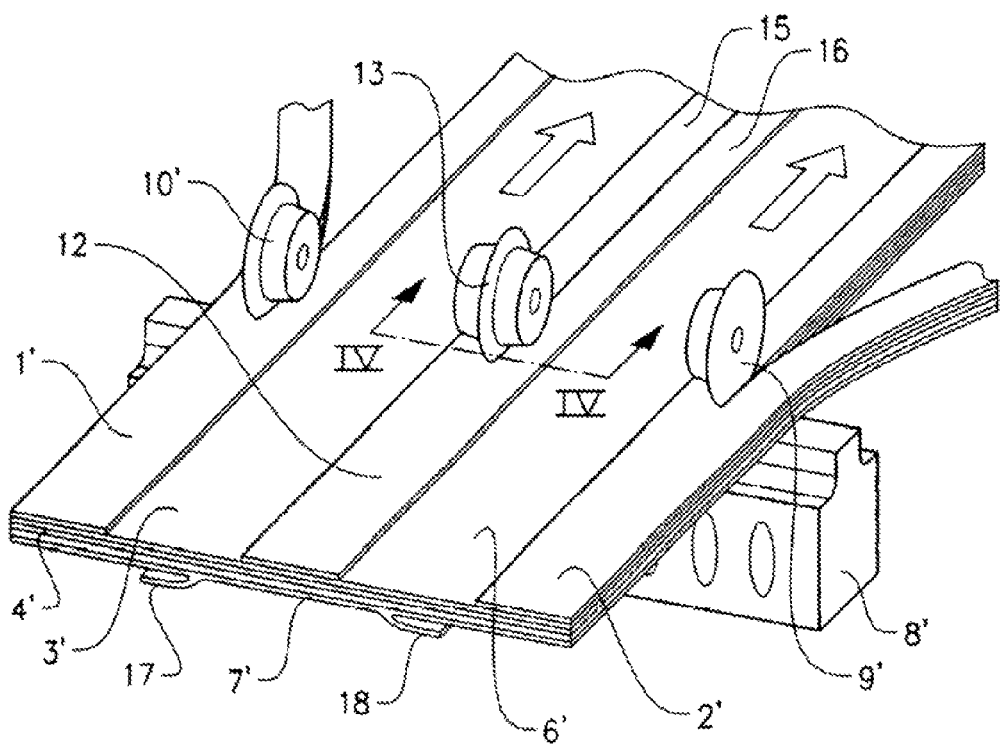
Figure 4:
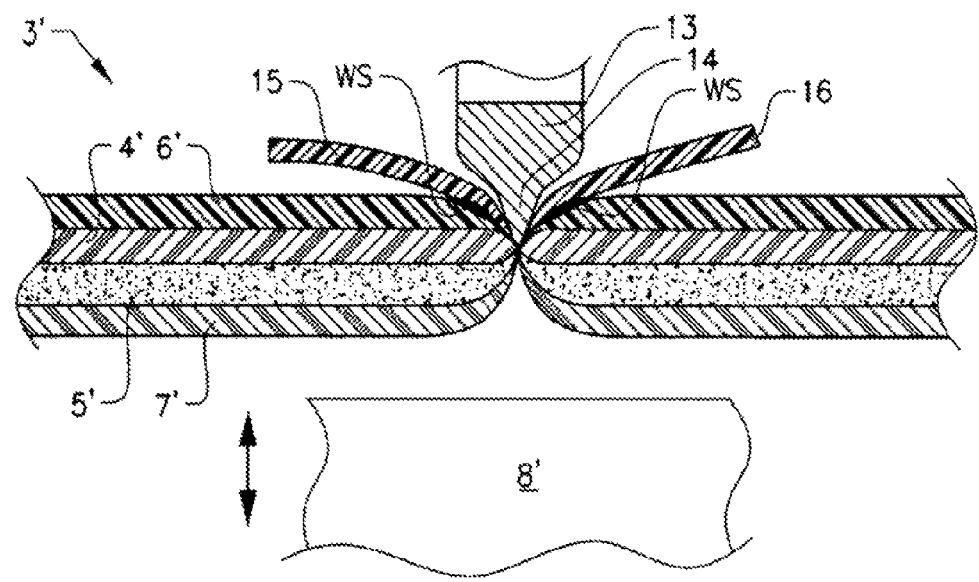

In FIGS. 3 and 4 a second embodiment is schematically illustrated in views similar to FIGS. 1 and 2. This embodiment differs from the embodiment described with reference to FIGS. 1 and 2 mainly in that the film dressing web is cut into two separate parts in order to produce film dressings having a transverse dimension smaller than the film dressing web 3' and in that grip tabs 15,16 are affixed to the adjacent edges of these two separate parts. Components in the embodiment according to FIGS. 3 and 4 corresponding to similar components in the embodiment according to FIGS. 1 and 2 are given the same reference numerals with the addition of a prime sign. In the method illustrated in FIGS. 3 and 4, a strip 12 is laid onto film dressing web 3' extending in the machine direction in the middle of film dressing web 3' simultaneously with strips 1' and 2' extending along the edges of web 3'. The web 3' with applied strips 1',2' and 12 is then passed through an ultrasound welding device having a horn 8' and counter rollers 9',10' and 13. The counter rollers 9',10' are similar to the counter rollers 9,10 described with reference to FIGS. 1 and 2 whereas counter roller 13 differs from rollers 9',10' by having larger dimension in a transverse direction relative to the machine direction and by having the flange 14 located in the middle of the roller as seen in the transverse direction. Thereby, a weld seam WS' affixing strip 12 to the carrier 6' is produced on both sides of the cutting line obtained due to the flange 14 and the strip 12 is divided into two parts extending along the adjacent edges of the two parts of web 3' produced by the cutting line. In all other aspects, the method of the embodiment according to FIGS. 3 and 4 correspond to the embodiment according to FIGS. 1 and 2.

Depending on the dimension of web 3' and the desired dimension of the produced film dressings more than one strip 12 can be applied. The numbers of counter rollers 13 in the ultrasound welding device must of course correspond to the number of strips 12 applied.

As is evident from FIG. 3, the release layer 7' is built of three parts whereby grip tabs 17 and 18 are provided by bending the inner longitudinal edge portions of the two outer parts and by letting the opposite longitudinal edge portions of the middle part extend over said bents portions. Such grip tabs should of course be located outside of cutting lines made by the ultrasonic welding device.

In the embodiment according to FIGS. 3 and 4, film dressings having the same transverse dimension are produced. However, it is possible to vary the transverse dimension of the produced film dressings by application of the strip 13 away from the middle of the film dressing web 3'.

In the shown embodiments the counter roller of the ultrasound welding device are located on the same side as the strips attached to the carrier layer and the horn is located on the same side as the release layer. This is however not necessary, the method will function also if the counter rollers and horn changes locations.

In the shown embodiments the film dressing web 3,3' have its carrier layer upwards but it is possible to produce this web and attach the strips with the web turned upside down in relation to the position shown in the drawings.

The described embodiments of the method can be modified without leaving the scope of the invention. The portions of the strips extending inwards over the carrier layer need not have straight edges but can have curved edges, which is preferred if the grip tabs only extend along a part of the length of the edge of a produced dressing. The portions of strips may also be discreetly affixed to the film, i.e. not cover along the complete edge. Furthermore, the grip tab need not be present on both of two opposite sides of the carrier layer but can be present only on such edge. However, it is preferred that grip tabs are present on both of two opposite sides and if the film dressing web is divided into several parts this is a must. The scope of invention should therefore only be limited of the content of the enclosed patent claims.

What is claimed is:

1. A film dressing comprising:
    a film layer on a first side coated with adhesive;
    a carrier layer releasably attached to the film layer on a second side thereof being opposite to the first side;
    a release layer releasably attached to the adhesive coating; and
    a first grip tab being affixed to an outer first edge of the carrier layer by a first welded seam having its outermost part in line with the outer first edge of the carrier layer, wherein the first welded seam has a width that is less than 1 mm, wherein the first grip tab extends inwardly over the carrier layer from the outer first edge of the carrier layer, wherein at least a portion of the first grip tab extending inwardly over the carrier layer is not affixed to the carrier layer, wherein the film layer, the carrier layer and the release layer have dimensions that are the same.

2. The film dressing of claim 1, further comprising a second grip tab, wherein the second grip tab is affixed to an outer second edge of the carrier layer by a second welded seam having its outermost part in line with the outer second edge of the carrier layer, wherein the second welded seam has a width that is less than 1 mm, wherein the second grip tab extends inwardly over the carrier layer from the outer second edge of the carrier layer, wherein at least a portion of the second grip tab extending inwardly over the carrier layer is not affixed to the carrier layer.

3. The film dressing of claim 2, wherein each of the first and second grip tabs is made of a material that is the same material as the carrier layer.

4. The film dressing of claim 1, wherein the first grip tab is made of a material that is the same material as the carrier layer.

5. The film dressing of claim 1, wherein the carrier layer is made of polypropylene and the film layer is made of polyurethane.

6. The film dressing of claim 1, wherein the adhesive coating consists of silicone gel adhesive and the release layer consists of polyethylene.

7. A method of attaching a grip tab to at least one of two opposite edges of a releasable carrier layer of a film dressing web, said web includes a film layer coated with adhesive on a first side and a carrier layer releasably attached to the film layer on a second side thereof being opposite to the first side, wherein the film layer and the carrier layer have dimensions that are the same, wherein the method comprises:
    choosing a material for the carrier layer that is heat welding incompatible with the film layer;
    feeding said film dressing web in a machine direction;
    applying at least one first strip of a material that is heat welding compatible with the carrier layer along at least a part of an edge portion of at least one of the opposite sides of said web extending parallel to the machine direction; and
    affixing said at least one first strip to the carrier layer and simultaneously cutting away an outermost part of the web with the at least one first strip applied thereto by passing the web with the at least one first strip applied thereto through an ultrasonic welding device.

8. The method of claim 7, wherein the at least one first strip of material is continuous.

9. The method of claim 7, further comprising attaching a release layer of thermoplastic material to the adhesive coating on the film layer before the step of applying at least one first strip of material to the web.

10. The method of claim 7, further comprising:
    applying at least one second strip of a material that is heat welding compatible with the carrier layer between the two opposite edges of the carrier layer and extending parallel to the machine direction simultaneously with the application of the at least one first strip; and
    affixing the second strip to the carrier layer simultaneously with the affixing of the at least one first strip to the carrier layer, and simultaneously cutting the film dressing web by passing the web with said second strip applied thereto through the ultrasonic welding device, a cutting line in said second strip being located between the two opposite edges of said second strip and being parallel to the machine direction.

* * * * *